(12) United States Patent
Aubry et al.

(10) Patent No.: US 7,235,402 B2
(45) Date of Patent: Jun. 26, 2007

(54) SCALABLE BIOREACTOR CULTURE PROCESS AND SYSTEM FOR THE MATURATION OF CONIFER SOMATIC EMBRYOS

(75) Inventors: Dany Aubry, Outremont (CA); Jean Archambault, Ile Bizard (CA); Francine M. Tremblay, Cap Rogue (CA)

(73) Assignee: Universite Laval, Quebec (CA)

( * ) Notice: Subject to any disclaimer, the term of this patent is extended or adjusted under 35 U.S.C. 154(b) by 151 days.

(21) Appl. No.: 11/085,930

(22) Filed: Mar. 21, 2005

(65) Prior Publication Data

US 2005/0287660 A1    Dec. 29, 2005

Related U.S. Application Data

(63) Continuation of application No. 10/018,595, filed as application No. PCT/CA00/00532 on May 5, 2000, now abandoned.

(60) Provisional application No. 60/132,763, filed on May 6, 1999.

(51) Int. Cl.
  *C12N 5/00*  (2006.01)
  *C12N 5/02*  (2006.01)
  *C12N 1/02*  (2006.01)
(52) U.S. Cl. .................. 435/422; 435/420; 435/410; 435/431; 435/261
(58) Field of Classification Search .............. 435/422, 435/261, 431, 420, 410

See application file for complete search history.

(56) References Cited

U.S. PATENT DOCUMENTS

| 4,417,417 A | 11/1983 | Mehra-Palta |
| 4,447,534 A | 5/1984 | Moebus et al. |
| 4,532,142 A | 7/1985 | Dean |
| 4,857,464 A | 8/1989 | Weathers et al. |
| 4,921,799 A | 5/1990 | Kitaura et al. |
| 5,043,283 A | 8/1991 | Endo et al. |
| 5,119,588 A | 6/1992 | Timmis et al. |
| 5,246,854 A | 9/1993 | O'Brien et al. |

(Continued)

FOREIGN PATENT DOCUMENTS

EP    0 431 464 A1    6/1991

(Continued)

OTHER PUBLICATIONS

Dilorio, A.A. et al. "Growth of Transformed Roots in a Nutrient Mist Bioreactor: reactor performance and evaluation" Applied Microbiol. Biotechnol. 37:457-462 (1992).

(Continued)

*Primary Examiner*—Kent Bell
(74) *Attorney, Agent, or Firm*—Darby & Darby

(57) ABSTRACT

A bioreactor culture system and process for producing conifer somatic embryos comprise a closed vessel, a biomass immobilization matrix, a liquid culture medium recirculating equipment, and a gas control equipment. The biomass immobilization matrix is installed in a closed vessel, a liquid culture medium is introduced in the closed vessel, and the level of liquid culture medium in the closed vessel is kept lower than the biomass immobilization matrix. The liquid culture medium recirculating equipment sprays liquid culture medium from the closed vessel onto the biomass immobilization matrix to thereby irrigate the maturing immobilized biomass.

16 Claims, 2 Drawing Sheets

U.S. PATENT DOCUMENTS

| | | | |
|---|---|---|---|
| 5,409,834 | A | 4/1995 | Birdwell |
| 5,413,928 | A | 5/1995 | Weathers et al. |
| 5,491,090 | A | 2/1996 | Handley et al. |
| 5,677,185 | A | 10/1997 | Handley, III |
| 6,087,176 | A * | 7/2000 | Durzan et al. .............. 435/431 |
| 6,417,001 | B2 | 7/2002 | Aitken-Christie et al. |
| 6,753,178 | B2 * | 6/2004 | Adelberg et al. ........... 435/261 |

FOREIGN PATENT DOCUMENTS

| | | |
|---|---|---|
| JP | 59-045879 | 3/1984 |
| JP | 59-059187 | 4/1984 |
| JP | 61-139381 | 6/1986 |
| JP | 01-074981 | 3/1989 |
| JP | 02-257811 | 10/1990 |
| JP | 02-284694 | 11/1990 |
| WO | WO-96/37096 A1 | 11/1996 |

OTHER PUBLICATIONS

Weathers, P.J. et al. "Regeneration of plant using nutrient mists." In Vitro 24:727-732 (1988).

Archambault J., Volesky B. and Kurz, W. G. W. "Surface Immobilization of Plant Cells" Biotechnology and Bioengineering 33, 293-299 1989.

Kessell R.H.J. and Carr A.H. 1972, The effect of dissolved oxygen concentration on growth and differentiation of carrot (*Daucus carota*) tissue, J. Exp. Bot. 23, 996-1007.

Greidziak V., Diettrich B. and Luckner M. 1990. Batch cultures of somatic embroys of *Digitalis Ianata*in gaslift fermenters. Development and cardenolide accumulation. Planta Med. 56, 175-178.

Chen T.H.H., Thompson B.G. and Gerson D.F. 1987, In vitro production of alfalfa somatic embryos in fermentation systems. J. Ferment. Technol, 65, 353-357.

Stuart D.A., Strickland S.G. and Walker K.A. 1987. Bioreactor production of alfalfa somatic embryos. Hortscience. 22, 800-803.

Jay V., Genestier S. and Courduraux J.C. 1992, Bioreactor studies on the effect of dissolved oxygen concentrations on growth and differentiation of carrot (*Daucus carota*L) cell cultures, Plant Cell Rep. 11, 605-608.

Molle F. Dupuis J.M., Ducos J.P., Anselm A., Crolus-Savidan I., Petiard V. and Freyssinet G. 1993, Carrot somatic embryogenesis and its application to synthetic seeds, pp. 257-287. In: K. Redenbaugh (ed.), Synseeds, Application of Synthetic Seeds to Crop Improvement. CRC Press, Boca Raton, FL.

Jolicoeur M., Chavarie C., Carreau P.J. and Archambault J. 1992, Development of a helical-ribbon-impeller bioreactor for high density plant cell suspension culture. Biotechnol. Bioeng. 39, 511-521.

Archambault J., Williams, R.D., Lavoie, L., Pepin, M.F. and Chavarie, C. 1994, Production of Somatic Embryos in a Helical Ribbon Impeller Bioreactor, Biotechnology and Bioengineering, 44, 930-943.

Attree, S., M., Pomeroy, M.,K. and Fowke, L.C. 1994, Production of vigorous, desiccation tolerant white spruce (*Picea glauca*[Moench.] Voss.) synthetic seeds in a bioreactor. Plant Cell Reports, 13, 601-606.

Attree, S.M., Moore, D., Sawhney, V.K. and Fowke, L.C. 1991, Enhanced maturation and desiccation tolerance of white spruce (*Picea glauca*Moench) somatic embryos: Effect of a non-plasmolsysing water stress and abscisic acid. Annals of Botany 68, 519-525.

Tremblay, L. and Tremblay, F.M. 1991, Carbohydrate requirements for the development of black spruce (*Picea mariana*(Mill.) B.S.P.) and red spruce (*Picea rubens*Sarg.) somatic embryos. Plant Cell, Tissue and Organ Culture 27, 95-103.

Tremblay L., and Tremblay, F.M. 1995, Somatic embryogenesis in black spruce (*Picea mariana*(Mill.) B.S.P.) and red spruce (*Picea rubens*Sarg.) somatic embryos. Biotechnology in Agriculture and Forestry, vol. 30; Somatic embryogenesis and synthetic seed I, pp. 431-445.

Tremblay, L, and Tremblay, F.M. 1995, Maturation of black spruce somatic embryos: Sucrose hydrolysis and resulting osmotic pressure of the medium. Plant Cell, Tissue and Organ Culture, 42, 39-46.

Attree, S.M., Moore, D., Sawhney, V.K. and Fowke, L.C: 1991, Enhanced maturation and desiccation tolerance of white spruce (*Picea glauca*Moench) somatic embryos: Effect of a non-plasmolsysing water stress and abscisic acid. Annals of Botany 68, 519-525.

Khlifi, S. and Tremblay, F.M. 1995, Maturation of black spruce somatic embryos. Part I. Effect of L-glutamine on the number and the germinality of somatic embryos. Plant Cell, Tissue and Organ Culture, 10, 1-11.

Tremblay, L. and Tremblay, F.M. 1991, Effect of gelling agents, ammonium nitrate, and light on the development of *Picea mariana* (Mill) B.S.P. (black spruce) and *Picea rubens* Sarg. (red spruce) somatic embryos. Plant Science, vol. 77, pp. 233-242.

Archambault J., et al., "Surface immobilization of plant cells", Biotechnology and Bioengineering, 1989, vol. 33, pp. 293-299.

Archambault, J., et al., "Development of Bioreactors for the Culture of Surface Immobilized Plant Cells", Biotechnology and Bioengineering, 1990, vol. 35, pp. 660-667.

Archambault J., "Large Scale (20L) Culture of Surface Immobilized *Catharanthus roseus* Cells", Enzyme Microbial Technology, 1991, vol. 13, pp. 882-892.

Patent Abstracts of Japan, JP 61-139381, Mitsui Petrochem Ind. Ltd., Jun. 26, 1986.

Patent Abstracts of Japan, JP 59-045879, Nitto Electric Ind. Co. Ltd., Mar. 13, 1984.

Patent Abstracts of Japan, JP 59-059187, Meiji Milk Prod. Co. Ltd., Apr. 4, 1984.

Patent Abstracts of Japan, JP 02-284694, Morita KK, Nov. 22, 1990.

Patent Abstracts of Japan, JP 01-074981, Babcock Hitachi KK, Mar. 20, 1989.

Patent Abstracts of Japan, JP 02-257811, Hitachi Reinestu KK, Oct. 18, 1990.

* cited by examiner

SCALABLE BIOREACTOR CULTURE PROCESS AND SYSTEM FOR THE MATURATION OF CONIFER SOMATIC EMBRYOS

CROSS-REFERENCE TO RELATED APPLICATION

This application is a continuation of U.S. patent application Ser. No. 10/018,595, filed Jun. 5, 2002 now abandoned, which is the national phase of International Patent Application No. PCT/CA00/00532, filed May 5, 2000, which claims the benefit of U.S. Provisional Patent Application No. 60/132,763, filed May 6, 1999. The prior applications are hereby incorporated by reference in their entirety.

FIELD OF THE INVENTION

The present invention relates to a scalable bioreactor culture process and system for the maturation of conifer somatic embryos under controlled conditions.

BRIEF DESCRIPTION OF THE PRIOR ART

Conifers species, and particularly spruce (*Picea*), pine (*Pinus*) and larch (*Larix*) species, are worldwide spread. They are generally harvested for the production of pulp, paper and timbers, which explains their economical importance. The Canadian forest industry is mainly based on these slow growing tree species, in particular black spruce (*Picea mariana*). To protect and ensure renewal of this natural resource, reforestation programs have been developed in Canada and in other countries like Sweden, Australia, New Zealand and the United States. The main objectives of these programs are the selection of fast growing cultivars and species by various improvement methods and the development of large scale propagation techniques to meet reforestation needs.

In this context, somatic embryogenesis represents the most attractive propagation technique allowing for:

(1)—rapid production of large numbers of clones of given elite cultivars; in fact, somatic embryogenesis is the only propagation method which can yield mass production of trees from a specific, possibly genetically altered, plant cell line;
(2)—asexual reproduction of selected and improved species with minimal genetic drift;
(3)—unlimited production of plantlets using in vitro techniques; and
(4)—selected and recombinant plant cell lines that can be cryopreserved and maintained for years in their original, juvenile state for future mass propagation and clonal testing.

Somatic embryogenesis of conifer species was first reported for *Picea abies* in 1985. Since that time, somatic embryogenesis has been demonstrated for more than 35 different conifer species. This technique is the most recent propagation method studied for conifer. However, industrial scale-up production of conifer somatic embryos in bioreactors has not been achieved at this time because of the lack of efficient and scalable culture systems.

Since its discovery in 1958, somatic embryogenesis has been recognized for its tremendous potential for mass propagation of plants and trees. This biological process results from the culture and differentiation in vitro of (somatic) plant cells into embryos (asexual reproduction) as compared to zygotic embryos contained in natural seeds (sexual reproduction). Somatic embryos (SE) obtained from a specific cell line are genetically identical and, consequently, yield plantlet clones. The production of artificial seeds from somatic embryos has been suggested for some time but has yet to be commercialized mostly because of the variable quality of somatic embryos and the poor encapsulation techniques currently in use.

Even though somatic embryo cultures have been generated for more than one hundred plant species, our knowledge about this complex differentiation process is limited. These cultures display numerous problems, including lack of synchrony, high heterogeneity, abnormal embryo and plant development, precocious germination and lack of quiescence induction and low conversion into normal plants (typically <30–70%). Most of these difficulties have been ascribed to the inherent high developmental plasticity of these delicate structures, making somatic embryos highly sensitive to their culture protocol. The choice and treatment of the original explant tissue, the procedures for the generation and maintenance of cell lines, the physico-chemical culture conditions of the growth and production (differentiation/maturation) phases all determine process feasibility.

Somatic embryos can be produced using solid and liquid cultures. Liquid systems offer numerous technical advantages over solid cultures, including better uniformity, efficiency and control of the culture process and easier scale-up of production. However, this remains to be demonstrated in practice. High production rates, of up to 900 to 6500 $SE.mL^{-1}$ of liquid culture in 15–20 days have been claimed for *Daucus carota*. These results, however, should be examined with caution on the basis of volumetric production, true mature somatic embryo (torpedo shape), homogeneity and conversion into plants. Still, more realistic effective production rates ($\approx$50–300 true embryos.$mL^{-1}$ in 15–30 days of culture) could prove to be commercially interesting for a certain number of plants and tree species. This could be achieved efficiently and economically in laboratory-to-pilot scale ($\approx$2–100-L) bioreactors.

Many studies for the improvement of somatic embryo cultures have been directed to the generation, selection and maintenance of embryogenic cell lines, inoculum sieving and medium formulation. The effect of the physical culture system on this delicate biological process has not been closely examined. Solid cultures are heterogeneous and limited by nutrient diffusion. Agitated liquid cultures, on the other hand, involve mainly faster, more uniform and controllable mass transfer processes. In this last case, the key issues are mixing shear, concentration and viscosity of the plant cell biomass or organ cultures and gas transfer rates, balance and concentration.

The few studies published on somatic embryo production in bioreactors centered mostly on liquid systems. They showed unclear results and patterns. Kessell R. H. J. and Carr A. H. 1972, The effect of dissolved oxygen concentration on growth and differentiation of carrot (*Daucus carota*) tissue. J. Exp. Bot. 23, 996–1007, showed that a dissolved oxygen below a critical level of 16% of air saturation was essential for the production of *D. carota* somatic embryos in a 4-L mechanically stirred (90 RPM) bioreactor. Similarly, *Digitalis lanata* somatic embryos were best produced in a 5-L airlift bioreactor (0.5 VVM (volume of gas per volume of liquid per minute)) upon continuous decline of dissolved oxygen from 100% to 5% within 24 days [Greidziak V., Diettrich B. and Luckner M. 1990. Batch cultures of somatic embryos of *Digitalis lanata* in gaslift fermenters. Development and cardenolide accumulation. Planta Med. 56, 175–178]. Chen T. H. H., Thompson B. G. and Gerson D. F.

1987, In vitro production of alfalfa somatic embryos in fermentation systems. J. Ferment. Technol, 65, 353–357, compared the performance of six culture systems for alfalfa somatic embryos production. Mechanically agitated bioreactors generated excessive mixing shear causing the cultures' death. In an airlift bioreactor, the low production of somatic embryos was attributed to the high concentration of dissolved oxygen (>80%). Flask cultures (1-L spinner, 0.25-L and 2-L shake flasks) produced 9, 30 and 44 SE.mL$^{-1}$, respectively, with more than 80% conversion into plants. The same plant cell species cultured in a 2-L mechanically stirred bioreactor produced no somatic embryo at a low concentration of dissolved oxygen (~21% by surface aeration at 2VVM) but 80 SE.mL$^{-1}$ were obtained from a sparged (1.8 VVM) high dissolved oxygen concentration (>70%) culture [Stuart D. A., Strickland S. G. and Walker K. A. 1987. Bioreactor production of alfalfa somatic embryos. Hortscience. 22, 800–803]. In a further study, both airlift and mechanically stirred bioreactors yielded productions of 157 SE.mL$^{-1}$ and 112 SE.mL$^{-1}$ in 14 days as compared to 140–180 SE.$^{-1}$.mL for flask cultures. However, conversion into plants declined significantly from 70-90% to 30% and 2–3% for somatic embryos obtained from solid and liquid flask and bioreactor cultures, respectively.

Jay V., Genestier S. and Courduraux J. C. 1992, Bioreactor studies on the effect of dissolved oxygen concentrations on growth and differentiation of carrot (*Daucus carota* L) cell cultures, Plant Cell Rep. 11, 605–608, reported the production of *D. carota* somatic embryos in a 3-L mechanically stirred bioreactor operated at 50 to 150 RPM depending on biomass concentration. The two cultures reported were cultivated at constant dissolved oxygen concentrations of 10% and 100% of air saturation, respectively, using a controlled gas mixing system and a constant sparging rate of 0.09 VVM. They yielded 170 and 600 SE.mL$^{-1}$ after 20 days. Again, results from this study need to be assessed with care since only one somatic embryo count per culture, which included embryogenic aggregates of all developmental stages, was taken; biomass concentration and composition were not reported and both cultures were likely submitted to different mixing regimes. Similarly, [Molle F., Dupuis J. M., Ducos J. P., Anselm A., Crolus-Savidan I., Petiard V. and Freyssinet G. 1993, Carrot somatic embryogenesis and its application to synthetic seeds, pp. 257–287. In: K. Redenbaugh (ed.), Synseeds, Application of Synthetic Seeds to Crop Improvement. CRC Press, Boca Raton, Fla.] obtained ~1000 *D. carota* embryogenic clusters per mL in 20 days for shake flask cultures, with 40% torpedo shaped somatic embryos. They indicated easy scale-up of this production in a 10-L conventional stirred bioreactor with little effect of dissolved oxygen and mixing speed on its performance. Furthermore, they described a complex in-line filtration system linking two bioreactors to synchronize somatic embryo production and allow for their maturation. This process yielded much lower production levels (~3–15 SE.mL$^{-1}$).

More recently, the inventors showed that embryogenic *Eschscholtzia californica* cell cultures carried out in a helical-ribbon-impeller (HRI) bioreactor [Jolicoeur M., Chavarie C., Carreau P. J. and Archambault J. 1992, Development of a helical-ribbon-impeller bioreactor for high density plant cell suspension culture. Biotechnol. Bioeng. 39, 511–521] displayed markedly poor morphology upon increasing the mixing speed from 60 to 100 RPM [Archambault, J., Williams, R. D., Lavoie, L., Pépin, M. F. and Chavarie, C. 1994, Production of Somatic Embryos in a Helical Ribbon Impeller Bioreactor. Biotechnology and Bioengineering, 44, 930–943]. This result illustrates the high sensitivity of this type of culture to mixing conditions especially when considering that this impeller and bioreactor configuration is characterized by significantly lower mixing shear than most conventional bioreactors. Similarly, low rate sparging (0.05 VVM, $k_L$a~6h$^{-1}$) resulted in a low quality embryogenic culture. The negative effects of these operating conditions on this production were ascribed mainly to the low, but still excessive shear experienced by the embryogenic cells and/or embryogenic aggregates which partly inhibited the development of somatic embryos.

In the same study, it was also found that the main effect of the concentration of dissolved oxygen on this culture process seems to be nutritional. High dissolved oxygen conditions (>60% of air saturation) of flask and bioreactor cultures favored higher undifferentiated biomass production and associated faster nutrient uptake, than low dissolved oxygen (~10–20%) cultures, at the expense of slowly differentiating embryogenic cell clusters. Controlled low dissolved oxygen bioreactor cultures, on the other hand, resulted in limited undifferentiated biomass formation (<5%) and higher and more normal embryo production with lower precocious germination.

Consequently, it appears that the differentiation/maturation of plant cells into somatic embryos in liquid cultures is affected by the physics of the culture system, and in particular by mixing shear, dissolved oxygen concentration and, likely, gas transfer rates. However, the effects of these culture parameters are not fully assessed. They may be dependent on the culture system, medium formulation, plant species and/or cell line used. Similar effects may be expected for solid supported, gas phase cultures.

Somatic embryogenesis of conifer species differs from that of other plant and tree species in many aspects, including in the starting biological material made of already partly differentiated embryogenic tissues obtained from zygotic embryos. Furthermore, the maturation of these tissues into somatic embryos has never been achieved using submerged, (uncontrolled) liquid cultures. Consequently, in developing a bioreactor culture system for this production, the inventors had to take into account these limitations as well as the basic methodology presently used to carry out this bioprocess in laboratory.

Somatic embryogenesis of conifer species comprises five different phases. The first phase involves the generation (induction) of embryogenic tissues grown for a few weeks from zygotic embryos placed on a specific solid medium. The subsequent proliferation of this embryogenic tissue (immature embryos) is achieved by subculturing weekly biomass samples on fresh solid or liquid medium during the maintenance phase. For production, embryogenic tissue samples are placed on a different solid medium whereby the growth regulator 2, 4 dichlorophenoxyacetic acid is replaced with abscissic acid (ABA) and the sucrose concentration is raised to ≈60 g·L$^{-1}$. These conditions induce the maturation of embrogenic tissue into mature normal embryos. Thereafter, these embryos are placed into germination conditions allowing their development into plantlets. These plantlets are transplanted into soil, acclimatized to normal (dryer) environment and finally grown under conventional greenhouse conditions.

This production process is complex since the biological material involved is highly sensitive to its culture environment and the process comprises many delicate phases, some of which are well controlled (maintenance and germination) while others (maturation and acclimation) remain much less understood. Furthermore, industrial production of conifer somatic embryos requires solving a few additional problems, including the development of an efficient and scalable system for this difficult culture process.

The maturation phase represents the most difficult step of this production process, which has only been achieved using small scale solid cultures. No true maturation of conifer somatic embryos has been obtained form liquid, submerged cultures. Most research groups in this field carry out the maturation of conifer somatic embryos using gelled medium contained in small Petri dishes which yield less than 100 embryos per plate. A floating bed system has also been worked out for the maturation of conifer somatic embryos, whereas embryogenic biomass is placed on a matrix floating over a liquid medium [Attree, S., M., Pomeroy, M., K. and Fowke, L. C. 1994, Production of vigorous, desiccation tolerant white spruce (*Picea glauca* [Moench.] Voss.) synthetic seeds in a bioreactor. Plant Cell Reports, 13, 601–606]. The scale-up potential of this system is limited.

OBJECTS OF THE INVENTION

An object of the present invention is to provide an efficient bioreactor culture system and process for the production (maturation phase) of conifer somatic embryos in a monitored and controlled surface-immobilization bioreactor.

Another object of the present invention is to provide a scalable culture system and process which can be scaled up to industrial size to yield high production levels of good quality conifer somatic embryos using a well controlled environment. This represents a significant improvement over conventional production systems, which mostly rely on laboratory, labour intensive and uncontrolled small scale Petri dish type cultures, and results in easier further processing, such as desiccation and harvesting of somatic embryos.

SUMMARY OF THE INVENTION

More specifically, in accordance with the present invention, there is provided a bioreactor culture process for producing conifer somatic embryos, comprising the steps of installing a biomass immobilization matrix in a closed vessel, sterilizing the biomass immobilization matrix and the closed vessel, introducing a liquid culture medium in the closed vessel to immerse the biomass immobilization matrix, adding a given volume of cultured cells in the liquid culture medium, immobilizing the cultured cells onto the biomass immobilization matrix, reducing the level of liquid culture medium in the closed vessel to a level lower than the biomass immobilization matrix, and spraying liquid culture medium onto the biomass immobilization matrix to thereby irrigate the immobilized biomass.

The present invention also relates to a bioreactor culture system for carrying out the above described bioreactor culture process.

Advantageously, the concentration of oxygen in the gas phase of the closed vessel is controlled.

The objects, advantages and other features of the present invention will become more apparent upon reading the following non restrictive description of a preferred embodiment thereof, given by way of example only with reference to the accompanying drawings.

DETAILED DESCRIPTION OF THE PREFERRED EMBODIMENT

Figure 1A:
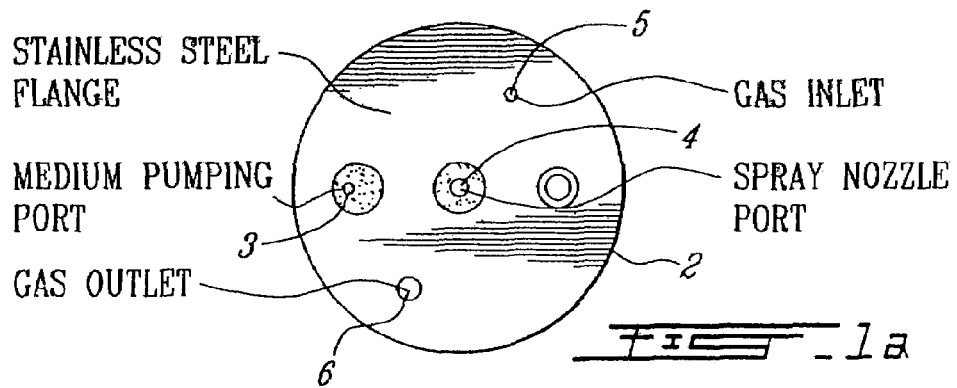
FIG. 1*a* is a top plan view of a bioreactor culture system according to the present invention.

Somatic embryogenesis is presently one of the most studied propagation methods for conifer species worldwide, which can best satisfy reforestation program needs. However, the growth and development of conifer somatic embryos are still poorly understood, and that is specially true for the maturation phase. The maturation of embryogenic tissue requires high sucrose concentration ($\geq 60$ g·L$^{-1}$), the presence of abscisic acid and some level of anhydrous stress applied to solid cultures [Attree, S. M., Moore, D., Sawhney, V. K. and Fowke, L. C. 1991, Enhanced maturation and desiccation tolerance of white spruce (*Picea glauca* Moench) somatic embryos: Effect of a non-plasmolsysing water stress and abscisic acid. Annals of Botany 68, 519–525] [Tremblay, L. and Tremblay, F. M. 1991, Carbohydrate requirements for the development of black spruce (*Picea mariana* (Mill.) B.S.P.) and red spruce (*Picea rubens* Sarg.) somatic embryos. Plant Cell, Tissue and Organ Culture 27, 95–103] [Tremblay L., and Tremblay, F. M. 1995, Somatic embryogenesis in black spruce (*Picea mariana* (Mill.) B.S.P.) and red spruce (*Picea rubens* Sarg.) somatic embryos. Biotechnology in Agriculture and Forestry, Vol. 30; Somatic embryogenesis and synthetic seed I, pp 431–445] [Tremblay, L, and Tremblay, F. M. 1995, Maturation of black spruce somatic embryos: Sucrose hydrolysis and resulting osmotic pressure of the medium. Plant Cell, Tissue and Organ Culture, 42, 39–46]. Other ongoing researches are focussing on other culture parameters, including the type of nitrogen and carbohydrate sources, and of gelling agent, and the light regime. However, these studies are not presently yielding additional information about the developmental behaviour of maturing conifer somatic embryos [Tremblay, L. and Tremblay, F. M. 1991, Carbohydrate requirements for the development of black spruce (*Picea mariana* (Mill.) B.S.P.) and red spruce (*Picea rubens* Sarg.) somatic embryos. Plant Cell, Tissue and Organ Culture 27, 95-103] [Tremblay L., and Tremblay, F. M. 1995, Somatic embryogenesis in black spruce (*Picea mariana* (Mill.) B.S.P.) and red spruce (*Picea rubens* Sarg.) somatic embryos. Biotechnology in Agriculture and Forestry, Vol. 30; Somatic embryogenesis and synthetic seed I, pp 431–445] [Tremblay, L, and Tremblay, F. M. 1995, Maturation of black spruce somatic embryos: Sucrose hydrolysis and resulting osmotic pressure of the medium. Plant Cell, Tissue and Organ Culture, 42, 3946][Khlifi, S. and Tremblay, F. M. 1995, Maturation of black spruce somatic embryos. Part I. Effect of L-glutamine on the number and the germinality of somatic embryos. Plant Cell, Tissue and Organ Culture, 10, 1–11] [Tremblay, L. and Tremblay, F. M. 1991, Effect of gelling agents, ammonium nitrate, and light on the development of *Picea mariana* (Mill) B.S.P (black spruce) and *Picea rubens* Sarg. (red spruce) somatic embryos. Plant Science 77, 233–242].

The maturation phase is mostly achieved on solid medium using Petri dishes and other small scale culture systems [Tremblay, L. and Tremblay, F. M. 1991, Carbohydrate requirements for the development of black spruce (*Picea mariana* (Mill.) B.S.P.) and red spruce (*Picea rubens* Sarg.) somatic embryos. Plant Cell, Tissue and Organ Culture 27, 95–103] [Tremblay L., and Tremblay, F. M. 1995, Somatic embryogenesis in black spruce (*Picea mariana* (Mill.) B.S.P.) and red spruce (*Picea rubens* Sarg.) somatic embryos. Biotechnology in Agriculture and Forestry, Vol. 30; Somatic embryogenesis and synthetic seed I, pp 431–445] [Tremblay, L, and Tremblay, F. M. 1995, Maturation of black spruce somatic embryos: Sucrose hydrolysis and resulting osmotic pressure of the medium. Plant Cell, Tissue and Organ Culture, 42, 39–46][Khlifi, S. and Tremblay, F. M. 1995, Maturation of black spruce somatic embryos. Part I. Effect of L-glutamine on the number and the germinality of somatic embryos. Plant Cell, Tissue and Organ Culture, 10, 1–11]. Recently, Attree, S. M., Pomeroy M. K. and Fowke L. C. 1994, Production of vigorous, desiccation tolerant white spruce (*Picea glauca* [Moench] Voss.) synthetic seeds in a bioreactor, Plant Cell Reports, 13, 601–606, developed a bioreactor system for producing white spruce somatic embryos, which involved placing embryogenic tissues on flat absorbent floating pads above a liquid medium contained in a 20-L glass bottle. This system produced ≈6000 somatic embryos (≈300 SE·L$^{-1}$). The scale-up potential of all these culture systems to industrial production levels remains limited.

In this context, the present invention uses a bioreactor for producing at large scale good quality conifer somatic embryos. Initially, efforts of the inventors were directed at inducing maturation of embryogenic tissues in liquid phase using a helical-ribbon-impeller bioreactor under controlled conditions as previously described [Archambault J., Williams R. D., Lavoie L., Pépin M. F. and Chavarie C. 1994, Production of Somatic Embryos in a Helical Ribbon Impeller Bioreactor. Biotechnology and Bioengineering, 44, 930–943]. Results showed that embryos development always stopped prior the cotyledon stage.

The inventors then investigated a second, more successful approach which involved the surface-immobilization technology developed by Archambault et al. [Archambault J., Volesky B. and Kurz, W. G. W. 1989, Surface immobilization of plant cells, Biotechnology and Bioengineering, 33, 293–299] for culturing undifferentiated plant cells. Initially, this technology was tested using flasks containing vertically hanging geotextile strips and operated according to two culture modes. In the first case, the strips were submerged in a liquid medium containing the embryogenic tissues. The cultures remained submerged and were agitated during all the experiment. The biomass attached well to the immobilizing matrix. Unfortunately, this culture mode resulted in the same developmental pattern as observed for suspension cultures i.e. with incomplete embryo formation.

The second operation mode tested involved the same flask-immobilizing strip arrangement and initial immobilizing procedure under submerged and agitated conditions for the first 24 hours of the culture. Thereafter, most of the liquid phase was removed and the flask was left standing with only the bottom of the strips in contact with the residual medium. After 4 to 6 weeks, normally shaped torpedo embryos formed on the immobilizing matrix. In view of these interesting results, this culture system was further tested in modified surface-immobilization bioreactors [Archambault J., Volesky B. et Kurts W. G. W 1990, Development of Bioreactors for the Culture of Surface Immobilized Plant Cells. Biotechnology and Bioengineering, 35, 660–667].

The present invention relates to an efficient and scalable bioreactor culture system for the production (maturation phase) of conifer somatic embryos. This bioreactor system uses the surface-immobilization technology which provides for optimal environmental conditions for this culture process. Key aspects of this culture system comprise:

(1)—the immobilization material, its unique properties and configuration and the mixing mode during the immobilization step in the culture vessel;

(2)—the easy, rapid, uniform and efficient attachment process of the embryogenic tissues to the immobilizing matrix under initial, short term flooding conditions;

(3)—the capacity to culture immobilized embryogenic tissues for maturation into normal somatic embryos under non flooding but controlled humidified and periodical nutrient supply conditions; these culture conditions are required to achieve efficient maturation of conifer somatic embryos;

(4)—the controlled spraying of solubilized nutrients; and (5)—the controlled gassing of the culture environment for best production.

Figure 1B:
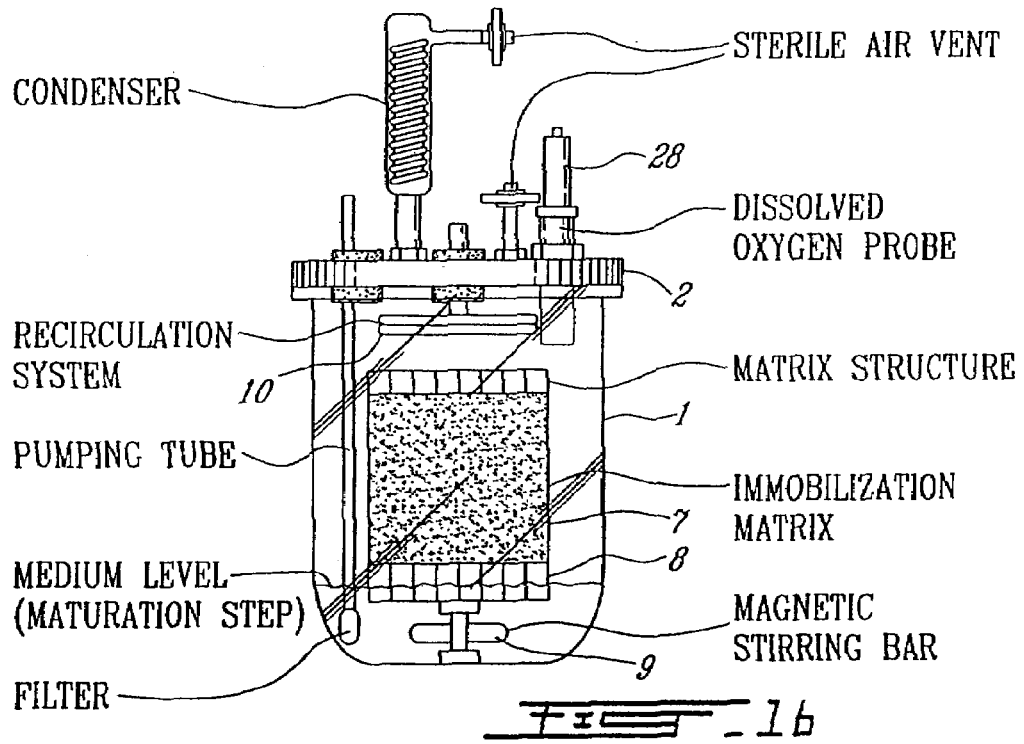
FIG. 1*b* is a side elevational view of the bioreactor culture system according to the present invention.
Figure 2:
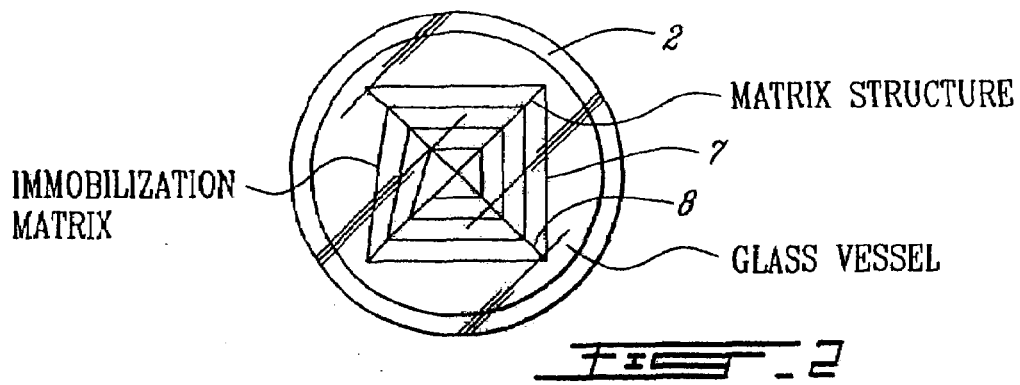
FIG. 2 is a top plan view of a glass vessel and immobilization matrix of the bioreactor culture system of FIGS. 1*a* and 1*b*.

Referring to FIGS. 1*a* and 1*b*, the bioreactor culture system is made of a 2-L glass vessel 1 equipped with a stainless steel top flange 2. In this flange 2, a medium pumping port 3, a spray nozzle port 4, a gas inlet 5 and a gas outlet 6 allow for medium feeding and recirculation, and gassing of the culture. An immobilization matrix 7 (FIGS. 1*b* and 2) is wrapped in a vertical spiral configuration on a stainless steel matrix holding structure 8 to optimize the surface-to-volume ratio of the system. This structure occupies a 1-L volume of the culture vessel 1 and yields an average immobilization surface of 1350 cm$^2$. The immobilization material is made of non-woven polyester short fibres. A raised magnetic stirring bar 9 (FIG. 1*b*) is located below the matrix holding structure 8 to provide for agitation during the immobilization step of the culture process.

Figure 3:
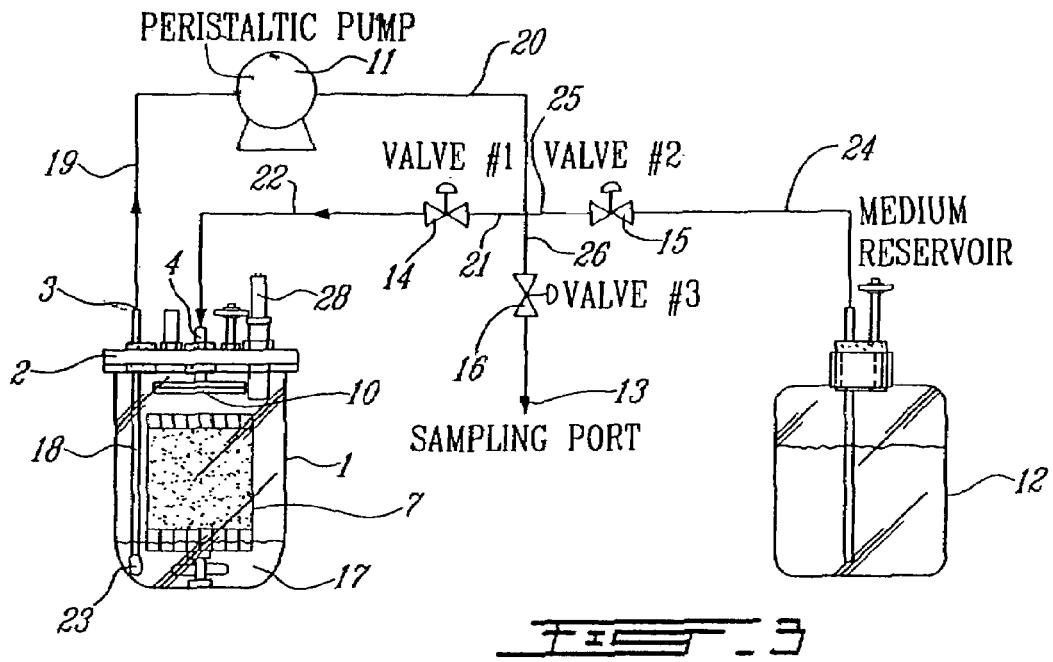
FIG. 3 is a schematic diagram illustrating the bioreactor culture system of FIGS. 1*a* and 1*b* having a liquid culture medium recirculating equipment.

FIG. 3 illustrates a liquid medium recirculation and spraying equipment of the bioreactor culture system according to the invention. This medium recirculation and spraying equipment is made of tubings, a spray nozzle 10 located above the matrix holding structure 8, a reversible peristaltic pump 11 with adjustable flow rate, a 2-L reservoir 12 for storing fresh liquid medium, a sampling port 13 and valves 14, 15 and 16. During the maturation step of the culture process, liquid culture medium 17 is pumped from the bottom of the glass vessel 1 to the spray nozzle 10. More specifically, peristaltic pump 11 pumps liquid medium 17 from the bottom of the glass vessel 1 through an inner generally vertical tube 18 extending through the stainless steel top flange 2, medium pumping port 3, and tube section 19 and supplies the pumped liquid medium 17 to the nozzle 10 through tube sections 20 and 21, valve 14 (valves 25 and 16 being closed), tube section 22 and spray nozzle port 4. The inlet of the inner tube 18 is equipped with a filter 23 to prevent the recirculation of free biomass which can plug the spray nozzle 10. Two spray nozzles were tested which yielded either mist or shower type sprays. The mist system resulted in more homogenous irrigation of the immobilization matrix 7 but the high viscosity of the sucrose concentrated medium prevented its use.

The liquid medium recirculation and spraying equipment is also used before the immobilization step to fill the glass vessel 1 with liquid culture medium from the 2-L reservoir 12. For example, the peristaltic pump 11 can be operated in the reverse direction to pump liquid medium from the reservoir 12 through tube section 24, valve 15, tube sections 25 and 20, and supplied to the glass vessel 1 through tube section 19, port 3, tube 18 and filter 23. The liquid medium recirculation and spraying equipment is further used as described in this paragraph, for injection of fresh liquid medium from the reservoir 12 during the maturation step of the culture process.

Figure 4:
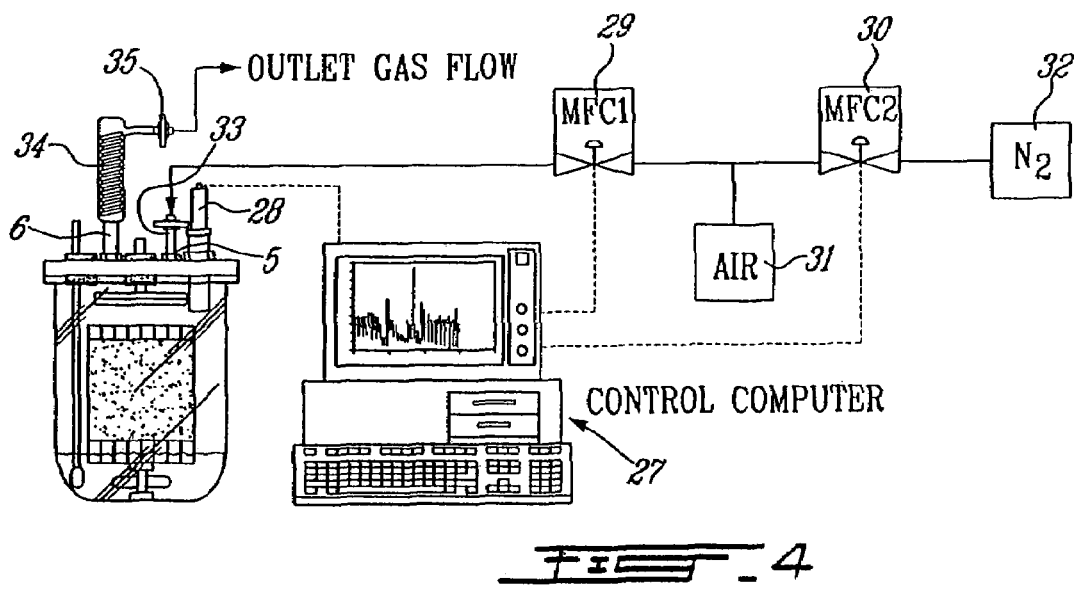
FIG. 4 is a schematic diagram illustrating the bioreactor culture system of FIGS. 1*a* and 1*b* having a gas control equipment.

After the immobilization step, the peristaltic pump 11 is used to pump liquid medium 17 from the glass vessel 1 to the reservoir 12 through filter 23, tube 18, port 3, tube section 19, tube sections 20 and 25, valve 15 (valves 14 and 16 being closed), tube section 24, to reduce the level of liquid medium 17 in the glass vessel 1 to the level shown in FIG. 1b, 3 and 4.

Finally, the peristaltic pump 11 can be used to take a sample of liquid medium 17 from the glass vessel 1 through the filter 23, tube 18, port 3, tube section 19, tube sections 20 and 26, valve 16 (valves 14 and 15 being closed) and sampling port 13.

The operation of the liquid medium recirculation and spraying equipment, for example the medium feeding/spraying rate, the opening and closure of the valves 14–16, turning on and off of the peristaltic pump 11, etc., can be controlled by a computer such as computer 27 in FIG. 4.

The gas control equipment of FIG. 4 comprises a control computer 27, a dissolved oxygen probe 28 located in the gas phase, a sterile air filter 33 two mass-flow controllers 29 and 30, a supply of air 31, a supply of nitrogen $N_2$, and a condenser 34. During the maturation step, the computer 27 measures the concentration of oxygen of the bioreactor's gas phase through the dissolved oxygen probe 28. This allows the computer 27 to control this concentration by manipulating the oxygen concentration of the air/nitrogen gas mixture supplied to the inlet 5 through the sterile air filter 33. The oxygen concentration is manipulated by the computer 27 through the mass-flow controllers 29 and 30 to thereby produce an air/nitrogen mixture having the desired oxygen concentration. The air/nitrogen mixture is injected at a constant flow rate into the bioreactor. The outlet gas flow from gas outlet 6 is cooled by the condenser 34, equipped with a sterile air filter 35, to minimize water losses by evaporation.

The bioreactor culture system is operated in two consecutive steps. Initially, the bioreactor is assembled with all accessories and immobilization matrix 7 and steam sterilized (121° C., 1 bar, 1 hour). During the immobilization step of the culture process, the sterile bioreactor is filled with liquid culture medium 17 and with the inoculum suspension of embryogenic tissues to an appropriate level above the immobilization matrix 7. An example of culture medium 17 is the following:

TABLE 1

LIQUID CULTURE MEDIUM

| Type | Name | Concentration | Sterilization mode |
|---|---|---|---|
| Major | $NH_4NO_3$ | 825 mg/L | Autoclave |
| | $KNO_3$ | 950 mg/L | Autoclave |
| | $MgSO_4 7H_2O$ | 925 mg/L | Autoclave |

TABLE 1-continued

LIQUID CULTURE MEDIUM

| Type | Name | Concentration | Sterilization mode |
|---|---|---|---|
| | $KH_2PO_4$ | 170 mg/L | Autoclave |
| | $CaCl_2 2H_2O$ | 11 mg/L | Autoclave |
| Minor | KI | 2.075 mg/L | Autoclave |
| | $H_3BO_3$ | 15.5 mg/L | Autoclave |
| | $MnSO_4 H_2O$ | 10.5 mg/L | Autoclave |
| | $Na_2MoO_4 2H_2O$ | 0.625 mg/L | Autoclave |
| | $CuSO_4 5H_2O$ | 0.25 mg/L | Autoclave |
| | $CoCl6H_2O$ | 0.065 mg/L | Autoclave |
| | $ZnSO_4 7H_2O$ | 21.5 mg/L | Autoclave |
| Iron | Sequetrene 330 Fe | 28 mg/L | Autoclave |
| Vitamins | Nicotinic acid | 0.5 mg/L | Autoclave |
| | Pyridoxine-HCL | 0.1 mg/L | Autoclave |
| | Thiamine-HCL | 0.1 mg/L | Autoclave |
| Hormones | Abscisic acid (ABA) | 80 µM | Filtration |
| Others | Casein hydrolysat | 1 g/L | Autoclave |
| | Myo-inositol | 100 mg/L | Autoclave |
| | L-Glutamine | 1 g/L | Filtration |
| | Sucrose | 60 g/L | Filtration |

Thereafter, this liquid phase is mixed under low shear conditions until all the biomass is attached to the immobilizing matrix 7, which generally occurs within the first 24 hours of the culture. At that time, most of the culture medium 17 is removed from the bioreactor, leaving a small volume of liquid below the immobilization matrix as shown in FIGS. 1b, 3 and 4 to maintain humid conditions in the culture vessel 1 and for periodical spray recirculation. This allows for maturation to occur under partly anhydrous conditions.

The maturation step of the process involves maintaining the immobilized, maturing biomass under sterile conditions with periodical recirculation and spraying of the residual liquid medium 17 contained in the bioreactor over the immobilization matrix 7 and continuous controlled gassing at low rate to maximize somatic embryos production. This generally lasts for 5 to 7 weeks until maturation of a maximum of the attached biomass.

The inoculum was prepared from embryogenic tissue biomass cultured in shake flasks for seven days using a proper maintenance liquid medium, for example the maintenance liquid medium of the following table 2:

TABLE 2

MAINTENANCE LIQUID MEDIUM

| Type | Name | Concentration | Sterilization mode |
|---|---|---|---|
| Major | $NH_4NO_3$ | 825 mg/L | Autoclave |
| | $KNO_3$ | 950 mg/L | Autoclave |
| | $MgSO_4 7H_2O$ | 925 mg/L | Autoclave |
| | $KH_2PO_4$ | 170 mg/L | Autoclave |
| | $CaCl_2 2H_2O$ | 11 mg/L | Autoclave |
| Minor | KI | 2.075 mg/L | Autoclave |
| | $H_3BO_3$ | 15.5 mg/L | Autoclave |
| | $MnSO_4 H_2O$ | 10.5 mg/L | Autoclave |
| | $Na_2MoO_4 2H_2O$ | 0.625 mg/L | Autoclave |
| | $CuSO_4 5H_2O$ | 0.25 mg/L | Autoclave |
| | $CoCl6H_2O$ | 0.065 mg/L | Autoclave |
| | $ZnSO_4 7H_2O$ | 21.5 mg/L | Autoclave |

TABLE 2-continued

MAINTENANCE LIQUID MEDIUM

| Type | Name | Concentration | Sterilization mode |
|---|---|---|---|
| Iron | Sequetrene 330 Fe | 28 mg/L | Autoclave |
| Vitamins | Nicotanic acid | 0.5 mg/L | Autoclave |
| | Pyridoxine-HCL | 0.1 mg/L | Autoclave |
| | Thiamine-HCL | 0.1 mg/L | Autoclave |
| Growth regulators | 2,4-Dichloro-phenoxyacetic acid (2,4-D) | 10 µM | Filtration |
| | Benzyl amino purine (BAP) | 5 µM | Filtration |
| Others | Casein hydrolysat | 1 g/L | Autoclave |
| | Myo-inositol | 100 mg/L | Autoclave |
| | L-Glutamine | 1 g/L | Filtration |
| | Sucrose | 10 g/L | Filtration |

The biomass from two to four flasks was harvested and filtered to a wet-to-dry biomass ratio of ≈60. The bioreactor cultures were inoculated to an initial biomass concentration varying from 5 to 20 g (grams) wet biomas weight per litre of culture medium. These innoculation conditions generally yielded an average 25% coverage of the immobilization matrix surface at the end of the immobilization step.

The following operating conditions yielded good production results. The cultures were gassed at a low flow rate of 25 mL.min$^{-1}$ to prevent excessive depletion of key metabolic gasses ($CO_2$ etc.). The oxygen concentration in the gas phase can be maintained at 21% (air) over the whole culture duration. However, more synchronous embryo development was observed when the oxygen concentration was dropped to 4.2% after the first week of maturation.

The medium recirculation and spraying equipment was only activated periodically to prevent biomass washing from the immobilization matrix 7 and to control the humidity level of the biomass. The following few operating conditions were tested with good results. The frequency, duration and recirculation flow rate were varied from one per hour to one per 4-hour cycles according to recirculation duration and flow rate, from 10 seconds to 4 minutes and from 45 to 325 mL. min$^{-1}$, respectively.

A 2-L bioreactor culture system was successfully experimented for the maturation and production of *Picea glauca* (white spruce) somatic embryos. Cultures of *Picea glauca* carried under appropriate operating conditions yielded production levels of 8000 to 12000 somatic embryos per experiment and per volume occupied by the immobilization structure (=1 L) after 6–8 weeks of culture (8 000 SE·L$^{-1}$). More than 90% of these embryos showed normal morphology and 90% of sampled somatic embryos germinated normally.

Scale-up of this culture system can be easily achieved using 6-L and 20-L surface-immobilization bioreactor systems which have already been developed and tested with success with various undifferentiated plant cell species [Archambauld, J., Volesky, B. et Kurz W. G. W. 1990, Development of Bioreactors for the Culture of Surface Immobilized Plant Cells. Biotechnology and Bioengineering 35, 660–667.] [Archambault J., 1991, Large Scale (20 L) Culture of Surface Immobilized *Catharanthus roseus* Cells. Enzyme Microbial Technology, 13, 882–892]. During this earlier work, it was found that the later larger systems were easier to operate and performed better than the 2-L version, especially for the initial and subsequent coverage of the immobilization matrix with biomass. Furthermore, spraying systems for these larger bioreactors will be easier to develop and operate as compared to the systems tested for the 2-L bioreactor.

The main application of this technology may be for large scale production of conifer plantlets used in reforestation programs. This novel bioreactor system allows mass production of high quality mature somatic embryos for conifer propagation, including of selected cultivars and genetically transformed species. This novel culture system can also be used to pursue research on the maturation phase of somatic embryo production. Its well controlled and monitored environment allows for the production of large quantities of potentially synchronized somatic embryos for subsequent treatments and studying on-line various aspects of the metabolic activities of maturing conifer somatic embryos, including their respiratory patterns, the effect of various gassing regimes, nutritional parameters, etc.

Examples will now be given in the following description:

EXAMPLE 1

A suspension of embryogenic tissues of white spruce (*Picea glauca*) was used as inoculum. These cultures were grown in 250 mL (milliliter) flasks containing a volume of 50 mL of suspension agitated at a speed of 90 rpm (revolutions per minute) under continuous light. The liquid culture medium used in maintenance phase is described in the above table 2. Three maintenance flasks grown for 6 days were harvested under sterile conditions for inoculation of the bioreactor. The filtered biomass was rinsed three times with a solution of sucrose (6%) to eliminate the presence of growth regulators (2,4-D) adversely affecting the development of somatic embryos. The biomass was then concentrated into a minimal volume and added to the bioreactor. A mass of 13 grams of humid biomass was inoculated under the form of a suspension, diluted in 2 L of culture medium which allowed total immersion of the immobilization matrix. The suspension was then gently agitated by means of a magnetic stirring bar during a period of 24 hours for immobilizing the biomass onto the matrix. After immobilization was completed, agitation was stopped and 1.8 L of the medium was withdrawn from the bioreactor. The remaining volume (200 mL) lied below the structure of the immobilization matrix. This inoculation and immobilization method was found suitable for all experiments. The maturation phase started with activation of the liquid medium recirculation and spraying equipment. In the first experiment, a medium spraying equipment was used to produce a plurality of high speed jets projected onto the inner wall of the bioreactor to spray the liquid culture medium. The liquid medium recirculation and spraying equipment was adjusted to maintain a sufficient but minimal humidity in the bioreactor. It was found that this last parameter has a strong influence on the development of the embryos. More specifically, the liquid medium recirculation and spraying equipment was turned on automatically every 2 hours during a period of 4 minutes at a flow rate of 80 cc/min. Air was supplied at a rate of 25 cc/min. Moreover, the 200 mL medium contained in the bioreactor was periodically replenished with 4 volumes of 100 mL of fresh medium during the 7 weeks of maturation. During the first 72 hours the matrix dried to reach an equilibrium point with automatic irrigation. With this species (*Picea glauca*), the biomass developed immature embryos during the first two weeks, i.e. the quantity of biomass increased before the development (maturation) of the somatic embryos began. During the third week organized nodules began to appear until mature embryos were obtained after 6 to 7 weeks of total culture duration. The development of embryos was practically synchronous. At harvest, 20% of the surface of the matrix was covered with biomass. A total amount of 110 grams of humid biomass was harvested, which corresponded to 6.7 grams of dry biomass, and 11 000 mature embryos (11 000 SE·L$^{-1}$) of which more than 90% were morphologically normal. The rate of germination under sterile condition was 90%.

EXAMPLE 2

A second culture was inoculated following the procedure of Example 1. A mass of 13 grams of humid biomass of *Picea glauca* was used for inoculating the bioreactor. The liquid medium recirculation and spraying equipment was the same as described in Example 1. The irrigation frequency was 4 minutes every 2 hours at a flow rate of 40 cc/min. A mixture of air and nitrogen was supplied to the bioreactor at a flow rate of 25 cc/min in order to obtain an oxygen concentration of 4.2%. This concentration of oxygen corresponds to 20% of the normal concentration of oxygen in air and, according to numerous publications, promotes development of somatic embryos versus growth of non embryogenic biomass. The 200 mL medium contained in the bioreactor was periodically replenished with 4 volumes of 100 mL of fresh medium during the 7 weeks of maturation. At harvest, a mass of 101 grams of humid biomass was collected, which corresponded to 12 000 mature somatic embryos (12 000 SE·L$^{-1}$) of which more than 70% were morphologically normal.

EXAMPLE 3

An liquid medium recirculation and spraying equipment of the "shower" type was used to obtain a more homogeneous irrigation. Drops of the liquid culture medium were randomly dispersed on the structure supporting the matrix. A mass of 12 grams of humid biomass (*Picea glauca*) from three flasks of maintenance culture of embryogenic tissues were used. Air was supplied at a flow rate of 25 cc/min during the first week of culture to promote development of the biomass and thereby increase the surface of the matrix covered with biomass. During the five last weeks of culture, a mixture of nitrogen and air was supplied to the bioreactor at a flow rate of 25 cc/min; the oxygen concentration of this mixture was 4.2% to promote maturation of the embryos. The automatic liquid medium recirculation and spraying equipment was operated during 4 minutes every 30 minutes at a flow rate of 80 cc/min, and the 200 mL medium contained in the bioreactor was periodically replenished with 5 volumes of 100 mL of fresh medium during the 7 weeks of maturation. Under these conditions, 15 000 mature embryos were harvested in a useful volume of 1 L, and 60% of these mature embryos were morphologically normal.

EXAMPLE 4

With the liquid medium recirculation and spraying equipment (irrigation equipment) of the "shower" type, a bioreactor was inoculated with 17 g (grams) of humid biomass of an embryogenic suspension of *Picea glauca*. The frequency of irrigation was fixed to 1 min every 2 hours at a flow rate of 280 cc/min. During the seven weeks of culture, air was supplied to the bioreactor at a flow rate of 25 cc/min. A volume of 100 mL of fresh replacement medium was injected in the 200 mL medium contained in the bioreactor after the third, fifth and sixth week. A total of 11 000 mature somatic embryos were harvested, and 60% of these mature embryos were morphologically normal.

EXAMPLE 5

The performance of the bioreactor was demonstrated by a series of 15 cultures conducted on white spruce (*Picea glauca*). Productivity of the bioreactor system could be easily increased by improving the inoculation procedure to increase the percentage of coverage of the immobilization matrix by the biomass and by optimizing the conditions of culture such as recirculation of the medium, replacement of used medium by fresh medium, control of the humidity of the matrix, and supply of gas.

Other cultures have been conducted on other conifer species. For example, embryogenic suspensions of black spruce (*Picea mariana*) cultured in maintenance in the same conditions as the suspensions of white spruce were used to inoculate the bioreactor. Two flasks containing a total of 5.5 g of humid biomass were used to inoculate the bioreactor. The inoculation was made in accordance with the methodology described in the preceding examples. Immobilization of the biomass on the matrix was complete after 30 minutes. Supply of liquid culture medium was made by a liquid medium recirculation and spraying equipment using high speed jets as described in examples 1 and 2. The recirculation flow rate was fixed to 75 cc/min during 10 seconds every 24 hours. This low irrigation level was compulsory since preliminary tests conducted using this species showed a higher sensitivity to humidity. No replacement of recirculated medium was made during the four weeks of culture. Air was supplied to the bioreactor at a constant flow rate of 50 cc/min. At harvest, less and 5% of the total surface of the matrix was occupied by the biomass. This is explained by a particular characteristic of this species which, during the maturation phase, produces almost no biomass and accordingly has covered only a small portion of the surface of culture. Nevertheless, total production of the bioreactor was 220 mature and morphologically normal embryos.

EXAMPLE 6

Another totally different species was tested with the bioreactor. Two flasks containing an embryogenic suspension in maintenance of hybrid larch (*Larix decidua*) was used for this culture. These flasks contained only 2 g of humid biomass. Immobilization of the biomass on the matrix was complete after a few hours of agitation. The liquid medium recirculation and spraying equipment was of the "spray" type. This liquid medium recirculation and spraying equipment was automatically operated every 24 hours during 10 seconds with a flow rate of 75 cc/min. No replacement of the recirculated medium was made during the culture. Air was supplied at a constant flow rate of 30 cc/min. After four weeks of maturation, 80% of the surface of the matrix was covered with biomass notwithstanding the low level of inoculation. About 35 mature embryos were harvested under culture conditions not optimized for this species. This shows the usefulness of the culture system and process to produce somatic embryos from most conifer species.

Although the present invention has been described hereinabove by way of a preferred embodiment thereof, this embodiment can be modified at will, within the scope of the appended claims, without departing from the spirit and nature of the subject invention.

What is claimed is:

1. A process for the mass production of mature conifer somatic embryos in a bioreactor comprising:
   (a) inoculating a suitable culture medium in said bioreactor with conifer embryogenic tissues;
   (b) immobilizing said embryogenic tissues onto a biomass immobilizing matrix contained in said bioreactor, under initial flooding conditions by mixing said culture medium and said embryogenic tissues under low shear conditions until said embryogenic tissues attach to said biomass immobilization matrix;
   (c) reducing the level of said culture medium in said bioreactor to a level such that only a lower end of said matrix or less, remains immersed in said medium; and
   (d) subjecting said attached embryogenic tissues to a maturation step under controlled minimal humidified conditions, thereby enabling mass production of mature conifer somatic embryos.

2. The process of claim 1, wherein said level of medium in (c) is reduced to a level below that of the biomass immobilizing matrix.

3. The process of claim 1, which further comprises:
   (a) installing a biomass immobilization matrix in a closed vessel of said bioreactor; and
   (b) sterilizing said biomass immobilization matrix and said closed vessel, prior to the inoculating step.

4. The process of claim 1, wherein the maturation step comprises:
   (a) maintaining an immobilized, maturing biomass under sterile conditions; and
   (b) spraying of a liquid medium over said immobilization matrix.

5. The process of claim 1, further comprising removing most of said culture medium between said immobilizing of said tissues and said maturation step.

6. A process for the mass production of mature conifer somatic embryos in a bioreactor comprising:
   (a) installing a biomass immobilization matrix in a closed vessel of said bioreactor;
   (b) sterilizing said matrix and said closed vessel;
   (c) introducing a suitable liquid culture medium in said closed vessel to immerse said matrix;
   (d) adding an inoculum suspension of conifer embryogenic tissues to said liquid culture medium;
   (e) mixing said liquid culture medium and said conifer embryogenic tissues under low shear conditions until said embryonic tissues attach to said immobilizing matrix and form an immobilized, maturing biomass;
   (f) removing most of said liquid culture medium;
   (g) maintaining said immobilized, maturing biomass under sterile conditions; and
   (h) spraying of a residual or replacement liquid medium over said immobilization matrix to provide minimum relative humidity, thereby enabling mass production of mature conifer somatic embryos.

7. The process of claim 1, further comprising periodical nutrient refreshment or replacement.

8. The process of claim 6, further comprising periodical nutrient refreshment or replacement.

9. The process of claim 1, further comprising gassing of said bioreactor at a controlled flow rate to maximize somatic conifer embryo production.

10. The process of claim 6, further comprising gassing of said bioreactor at a controlled flow rate to maximize somatic conifer embryo production.

11. The process of claim 1, further comprising harvesting and germinating the mature somatic embryos.

12. The process of claim 6, further comprising harvesting and germinating the mature somatic embryos.

13. The process of claim 1, wherein said immobilizing matrix has a vertical spiral configuration.

14. The culture of conifer somatic embryos of claim 1, wherein at least 60% of said mature somatic embryos are mature cotyledonary somatic embryos.

15. The culture of conifer somatic embryos of claim 1, wherein at least 70% of said mature somatic embryos are mature cotyledonary somatic embryos.

16. The process of claim 1, further comprising the step of partially drying said immobilization matrix to reduce humidity level following step c).

* * * * *